United States Patent [19]

Reese et al.

[11] Patent Number: 5,370,646

[45] Date of Patent: Dec. 6, 1994

[54] BONE CLAMP AND INSTALLATION TOOL

[76] Inventors: H. William Reese, 1940 E. Southern, Tempe, Ariz. 85282; Harry A. Pape, 70 Merram Rd., Princeton, Mass. 01541; G. Lawrence Thatcher, 77 Linwood St., Chelmsford, Mass. 01824

[21] Appl. No.: 977,074

[22] Filed: Nov. 16, 1992

[51] Int. Cl.⁵ ............................................. A61F 5/04
[52] U.S. Cl. .................................... 606/72; 606/60; 606/151; 606/139; 606/99; 606/104; 411/509; 411/913; 24/588
[58] Field of Search ................. 606/72, 75, 99, 104, 606/105, 53, 116, 117, 138, 142, 151, 139, 60; 24/16 PB, 19, 543, 524, 568, 588, 612; 411/338, 339, 509, 913

[56] References Cited

U.S. PATENT DOCUMENTS

| | | | |
|---|---|---|---|
| 887,074 | 5/1907 | Depage | 606/60 |
| 4,688,561 | 8/1987 | Reese | 606/72 |
| 4,884,572 | 12/1989 | Bays | 606/139 |
| 4,950,285 | 8/1990 | Wilk | 606/151 |
| 5,084,053 | 1/1992 | Ender | 606/104 |
| 5,207,694 | 5/1993 | Broome | 606/151 |
| 5,269,809 | 12/1993 | Hayhurst | 606/151 |

Primary Examiner—Robert A. Hafer
Assistant Examiner—David J. Kenealy
Attorney, Agent, or Firm—Antonio R. Durando; Harry M. Weiss

[57] ABSTRACT

A clamp and installation tool combination wherein the clamp portion comprises an elongated pin having a hook at both ends and containing multiple circumferential notches along its shaft. A clamp button with a central through-hole is mounted on the shaft of the pin and engages the notches so as to produce a ratchet-type mechanism that permits the motion of the button only in the direction of the distal end of the pin. The installation tool consists of a syringe-type applicator having an outer barrel containing a pin retention clip designed to engage the hook at the proximal end of the pin, so that the pin cannot move in relation to the barrel of the tool. A hollow inner piston having a longitudinal groove conforming to the size and shape of the retention clip is mounted slidably in the barrel and can be pushed forward to engage the clamp button and force it over the pin's circumferential notches toward the distal end of the pin with great pressure without affecting the stability of the coupling between the pin and the barrel of the tool. Thus, a bone clamp is formed by mounting the pin in the installation tool and inserting the distal end of the pin through an aperture formed within two or more parts of a bone until the distal hook protrudes and engages the back surface of the bone parts to form a distal anchor; the piston of the tool is then pushed forward to cause the clamp button to press against the front surface of the bone parts to provide a proximal anchor that completes the bone clamp. The excess portion of the pin is then cut and removed with the installation tool.

21 Claims, 3 Drawing Sheets

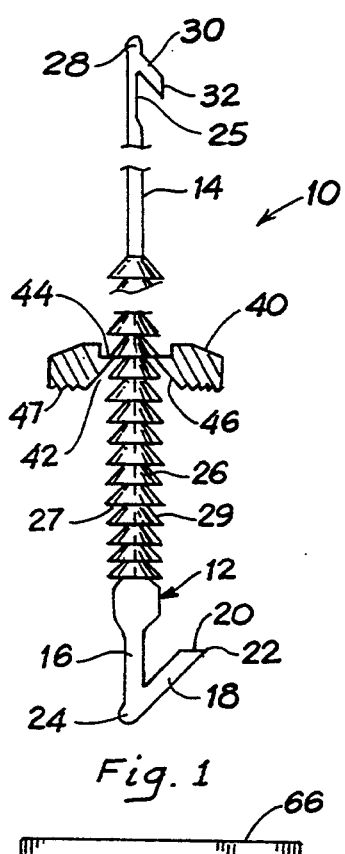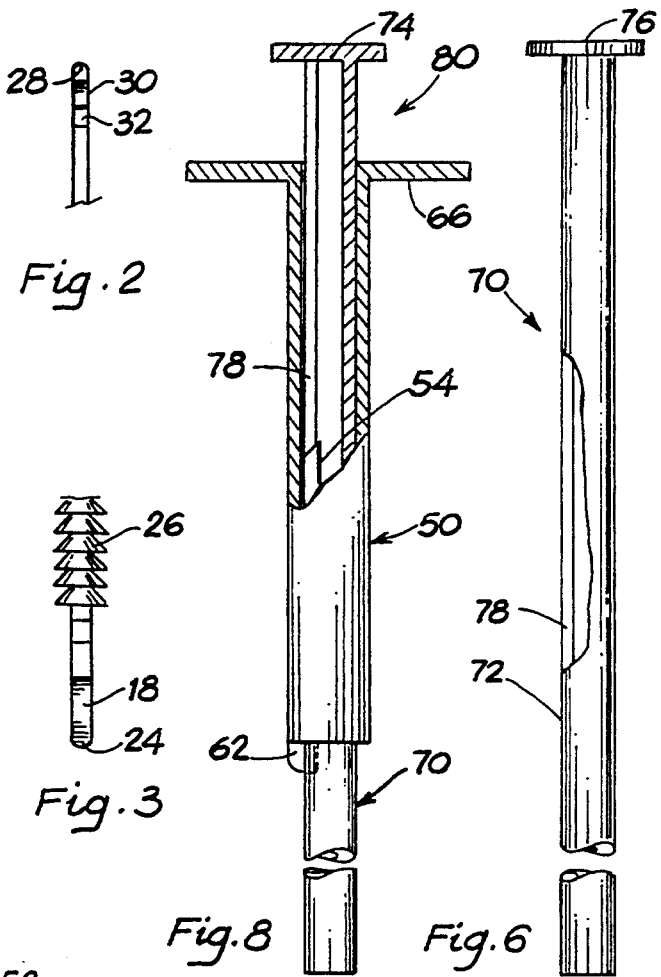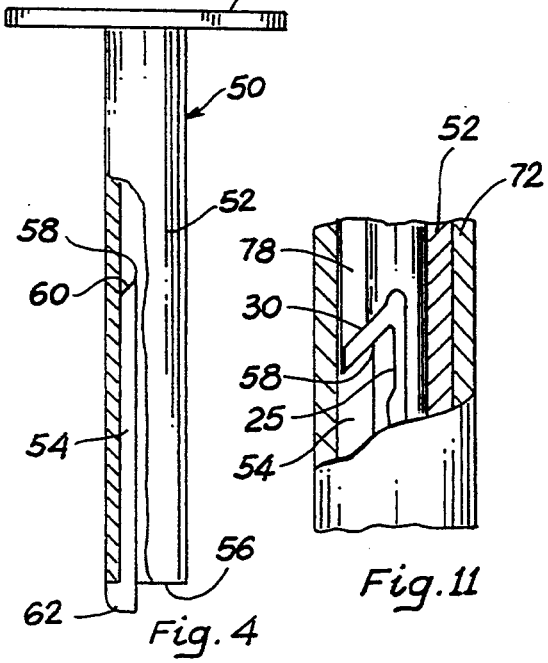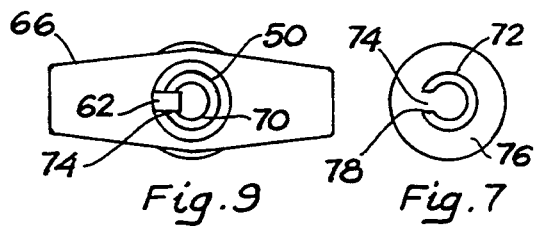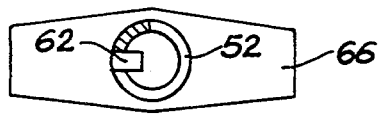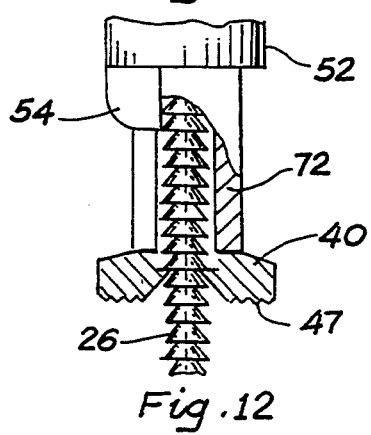

BONE CLAMP AND INSTALLATION TOOL

BACKGROUND OF THE INVENTION

1. Field of the Invention

This invention is related in general to the field of orthopedic devices and methods for joining fractured bones. In particulars the invention provides an improved pin-type bone-clamping device and an installation tool that permit the quick joining of fractured bones.

2. Description of the Related Art

When bones are either fractured by accident or severed by surgical procedure, the healing process requires that they be rejoined and kept together for lengthy periods of time in order to permit the recalcification and bonding of the severed parts. Accordingly, adjoining parts of a severed or fractured bone are typically clamped together or attached to one another by means of a pin or a screw driven through the rejoined parts. Movement of the pertinent part of the body is then kept at a minimum by a cast, brace or splint in order to promote healing and avoid mechanical stresses that may cause the bone parts to come apart during normal or necessary bodily activity.

The surgical procedure of attaching two or more parts of a bone with a pin-like device requires an incision in the tissue surrounding the bone and the drilling of a hole through the bone parts to be joined, often with little space to operate without inflicting further injury to the patient. Therefore, it is very important that the bone-clamp device used be capable of quick installation with a simple procedure. U.S. Pat. No. 4,796,612 (1988) and No. 4,903,692 (1990) to Reese describe a bone clamp and a corresponding installation tool that enable a surgeon to easily drive a pin through an aperture in two or more parts of a bone and lock it in place by means of a self-locking button placed around the shaft of the pin. The tip of the pin has a hook that engages the back surface of the bone after protruding through the aperture in the bone. The shaft of the pin features circumferential notches that engage the button in ratchet fashion, so that the button can be pushed against the front surface of the bone to anchor the pin in place, thereby clamping the severed bone parts together. The installation tool consists of a syringe-like structure comprising an outer barrel and a slidably-disposed hollow inner piston wherein the shaft of the pin is mounted prior to application. A retaining fork projecting inwardly from the distal and inside surface of the barrel engages the notches on the shaft of the pin and prevents the pin from moving freely in relation to the barrel. Through a longitudinal groove in which the retaining fork is slotted, the piston is free to slide inside the barrel and engage the button, which can thus be pushed forward along the shaft of the pin while the pin is held by the retaining fork so that the button is locked in place against the surface of the bone.

The Reese bone clamp and installation tool provide an efficient method for clamping fractured bones together, but the retaining fork mechanism described in U.S. Pat. No. 4,903,692 for coupling the pin to the barrel of the installation tool has been found to be unsatisfactory at times when relatively great pressure is required to push the self-locking button forward. This invention is directed at solving this problem by describing an improved coupling mechanism between the pin and the tool.

SUMMARY OF THE INVENTION

In view of the above-mentioned desirable features in bone clamps, one objective of this invention is the development of an improved means and method for clamping bones.

Another objective of the invention is a bone clamp and installation tool wherein the coupling mechanism is improved to permit greater pressure to be exercised on the piston of the tool without causing the release of the pin from the tool.

A further goal of the invention is an improved means and method for clamping bones wherein the clamp can be inserted through an aperture in one or more bones and locked firmly in place.

Yet another goal of the invention is a clamp that consists of only two components, a through pin and a clamp button, wherein the clamp action is obtained by tightening the button on the pill anchored to the bone, thus causing the button to lock tightly against the bone and form a clamp without further assembly.

Still another objective is a bone clamp that may be tightened to some degree even without passing the pin entirely through the bone parts that are being joined.

A further objective is a clamp that can be utilized not only to connect two bones, but also to cause soft tissue to adhere to the cortex of a bone.

A final objective is the easy and economical manufacture of the device according to the above stated criteria. This is achieved by using commercially available components and materials, modified only to the extent necessary to fit the requirements of the invention.

Therefore, according to these and other objectives, the present invention consists of a clamp and installation tool combination wherein the clamp portion comprises an elongated pin having a hook at both ends and containing multiple circumferential notches along its shaft. A clamp button with a central through-hole is mounted on the shaft of the pin and engages the notches so as to produce a ratchet-type mechanism that permits the motion of the button only in the direction of the distal end of the pin. The installation tool consists of a syringe-type applicator having an outer barrel containing a pin retention clip designed to engage the hook at the proximal end of the pin, so that the pin cannot move in relation to the barrel of the tool. A hollow inner piston having a longitudinal groove conforming to the size and shape of the pin shaft and capable of accommodating the retention clip is mounted slidably in the barrel and can be pushed forward to engage the clamp button and force it over the pin's circumferential notches toward the distal end of the pin with great pressure without affecting the stability of the coupling between the pin and the barrel of the tool. Thus, a bone clamp is formed by mounting the pin in the installation tool and inserting the distal end of the pin through an aperture formed within two or more parts of a bone until the distal hook protrudes and engages the back surface of the bone parts to form a distal anchor; the piston of the tool is then pushed forward to cause the clamp button to press against the front surface of the bone parts to provide a proximal anchor that completes the bone clamp. The excess portion of the pin is then cut and removed along with the installation tool.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIG. 1 is an elevational view of a partially cut-out clamp pin and partially sectioned clamp button of the preferred embodiment of the invention.

FIG. 2 is a right side view of the proximal end of the pin shown in FIG. 1.

FIG. 3 is a right side view of the distal end of the pin shown in FIG. 1.

FIG. 4 is an elevational, partially cut-away view of the barrel portion of the installation tool used in conjunction with the clamp pin and button illustrated in FIG. 1.

FIG. 5 is a bottom view of the barrel portion of the installation tool of FIG. 4.

FIG. 6 is an elevational, partially cut-away view of the piston portion of the installation tool used in conjunction with the clamp pin and button illustrated in FIG. 1.

FIG. 7 is a bottom view of the piston portion of the installation tool of FIG. 6.

FIG. 8 is an elevational, partially cut-away view of the combined piston and barrel portions of the installation tool used in conjunction with the clamp pin and button illustrated in FIG. 1.

FIG. 9 is a bottom view of the installation tool of FIG. 8.

FIG. 11 is an enlarged view of the portion of FIG. 10 illustrating the interlocking connection between the proximal hook of the clamp pin and the retention clip in the barrel of the invention.

FIG. 12 is another enlarged view corresponding to the portion of FIG. 10 illustrating the pushing action of the piston of the installation tool against the clamp button of the invention.

DESCRIPTION OF THE PREFERRED EMBODIMENTS

Figure 13:
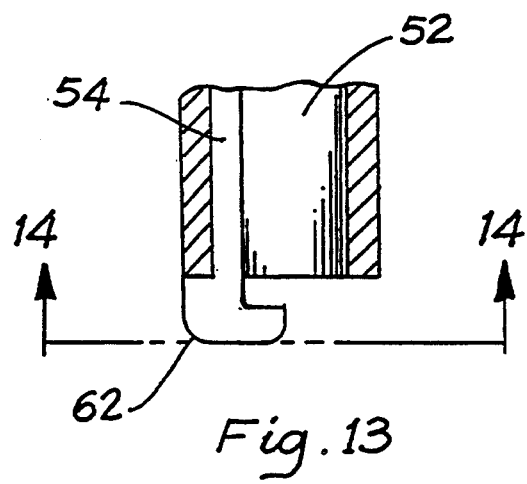
FIG. 13 is an enlarged cut-out view of another embodiment of the invention illustrating a retaining tab at the bottom end of the ridge in the barrel.

The most important inventive feature of this disclosure is a locking mechanism to firmly connect the bone clamp and installation tool described in the above referenced patents, so that great pressure can be exercised against the clamp button without causing the release of the clamp pin from the installation tool. Various other improvements are also disclosed that increase the clamping efficiency and versatility of the device. Inasmuch as the bone clamp and the installation tool described herein constitute direct improvements over the clamp device and tool disclosed in U.S. Pat. No. 4,796,612 and No. 4,903,692, respectively, those patents are herein incorporated by reference.

Referring to the drawings, wherein like parts are designated throughout with like numerals and symbols, FIG. 1 illustrates in elevation a partially cut-out and cross-sectional view of one embodiment 10 of the clamp pin and clamp button of this invention. The clamp pin 12 consists of a straight shaft 14 having a barb or hook at both ends, which will herein be referred to as distal and proximal with reference to the position of the pin with respect to the direction of insertion into a bone. The distal hook 16 consists of a resilient wing 18 forming an acute angle (preferably of approximately 45 degrees) with the distal tip of the pin 12, essentially having the same characteristics described in the referenced patent. In addition, the wing 18 has a substantially flat contact surface 20 normal to the longitudinal axis of the pin, thus providing a sharp edge 22 for contacting and firmly engaging the surface of the bone in the course of installing the clamp, as will be detailed below. Furthermore, at the tip of the hook 16, the wing protrudes slightly on the other side of the shaft 14 (opposite to the side of main portion of the wing 18) to form a rounded distal tip 24 substantially coaxial with the main axis of the wing 18.

Figure 18:
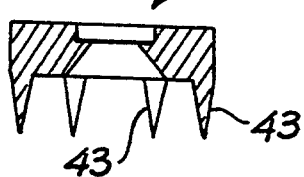
FIG. 18 is a cross-sectional view of a clamp button with spikes designed for use in clamping soft tissue to the cortex of a bone.

As in the embodiments described in the prior art, the distal portion of the shaft 14 features a plurality of resilient, peripheral notches 26, preferably substantially circumferential, having a flat surface 27 perpendicular to the axis of the shaft 14 facing the distal end of the shaft and a sloped conical surface 29 facing the proximal end of the shaft, so that each notch is capable of engaging a clamp button 40 through which the stem is threaded to permit a ratcheted motion of the button in the distal direction. The length of the shaft 14 covered by notches 26 may vary depending on the size of the bones to be clamped together; therefore, the shaft is illustrated in the figures in partially cut-out view. Although not critical to the invention, each notch 26 is preferably shaped like a longitudinal section of a cone having a smaller cross-section approximately the size of the shaft facing the proximal end and having a larger cross-section facing the distal end of the pin. Correspondingly, the clamp button 40 consists of an annular structure having a central through-hole or bore 42 with a resilient inner lip 44 capable of engaging the larger portion of each cone 26 to prevent the button from sliding in the proximal direction, but also capable of resiliently sliding over the sloped surface of each cone to move in step-wise ratchet fashion in the distal direction. This action can be obtained by having a lip 44 that has a flat surface facing the proximal end of the pin and a sloped surface 46, that conforms to the conical shape of the notches 26, facing the distal end of the pin. Friction bumps or spikes 47 may be added to the bottom surface of the clamp button 40 in order to increase its adhesion to the proximal surface of the clamped bone or bones. In addition, these spikes can also be used to clamp soft tissue against the bone. For this purpose, as illustrated in the clamp button 41 shown in FIG. 18, the spikes 43 are preferably sharp and placed along the periphery of the button for maximum clamping action on soft tissue against the bone.

Figure 14:
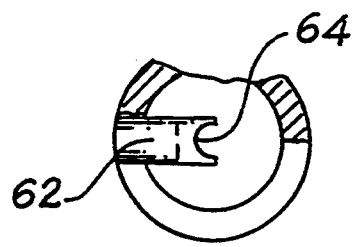
FIG. 14 is a view taken from line 14—14 in FIG. 13.

In what amounts to the major improvement of this clamp pin over the one described in the referenced patents, the proximal end of the clamp pin 12 also comprises a proximal hook 28 that consists of a rigid wing 30 forming an acute angle, preferably of approximately 45 degrees, with the shaft of the pin. The proximal hook 28 is preferably smaller than the distal hook 18 and the leg 25 of the hook 28, immediately distal to the tip of the hook, is preferably sized with a cross-section smaller than that of the shaft 14, thereby acquiring a resilience than that of the shaft and the wing. The resilience of the leg 25 enables the wing 30 to be folded shut to permit the insertion of the pin through the bore 42 of the clamp button 40; in addition, the resilience causes the leg 25 to bend under strain, rather than the wing 30, thereby rendering more secure the coupling of the hook 28 with the retaining clip 58, as detailed below. As also illustrated in FIGS. 2 and 3, the wing 30 is shown positioned in the same plane of the distal wing 18, but that configuration is not critical to the functioning of the invention. Similarly, the end of the wing 30 is illustrated as having a flat surface 32 parallel to the longitudinal axis of the pin in order to conform to the geometry of the installation tool, but that shape is also not critical so long as the hook 28 is capable of engaging a corresponding retention clip in the barrel of the installation tool without interfering with the free movement of the piston, as will be detailed below. The latter characteristic is critical to the proper functioning of the improved clamp of this invention. Referring to FIGS. 4 and 5, the barrel portion 50 of the installation tool 80 of the invention is shown in partially cut-away view. Much the same way as a syringe, the barrel 50 consists of a hollow cylindrical tube 52 containing a keel-like longitudinal ridge 54 protruding inward from the inside wall of the tube in the bottom portion of the barrel. At some distance from the bottom end 56 of the barrel, so as to be sufficiently long to provide stability to the clamp pin 12 after insertion into the barrel, the ridge 54 is truncated and forms a retaining clip 58 having a contact face 60 designed to cooperatively engage the wing 30 of the proximal hook 28, such as by forming an acute angle with the inside wall of the barrel conforming with the angle between the proximal wing and the shaft of the clamp pin (preferably 45 degrees). In the preferred embodiment of the invention, the length of the ridge 54 is approximately half the length of the barrel and it is sized to permit the full excursion of the clamp button 40 upon full depression of the piston 70 in the barrel 50. In another embodiment of the invention, shown in the partial view of FIGS. 13 and 14 and particularly illustrated in U.S. Pat. No. 4,903,692, a forked retaining tab 64 may be added to protrude inwardly at the distal tip 62 of the ridge 54 to provide a guide for the clamp pin 12. In that case, the notched area of the pin may be extended so that a notch 26 is engaged by the tab 64 to further increase the retaining action of the clip/tab combination. Finally, the barrel 50 comprises a pair of bosses or handle 66, which may be integral with the tube 52, for holding the installation tool with the index and middle fingers while depressing the piston with the thumb, in the same manner that a conventional hypodermic syringe.

FIGS. 6 and 7 show the piston portion 70 of the installation tool. It consists of a hollow shaft 72 with an outside diameter slightly smaller than the inside diameter of the tube 52, so that the two can be slidably connected, and with a longitudinal groove 74 sized to fit snugly around the internal longitudinal ridge 54 of the barrel portion 50. The piston portion 70 must be longer than the barrel portion 50 by an amount at least equal to the expected travel of the clamp button 40 during use. In the preferred embodiment of the invention, the piston is sufficiently long to push the clamp button all the way through the last notch in the distal portion of the pin 12. Thus, the barrel 50 and the piston 70 are slidably connected to form a syringe-type installation tool 80 wherein the piston protrudes from the bottom of the barrel, as illustrated in FIGS. 8 and 9. Finally, the piston 70 comprises a rounded push-knob 76, which may be integral thereto, for pushing the piston forward through the barrel portion 50.

Figure 10:
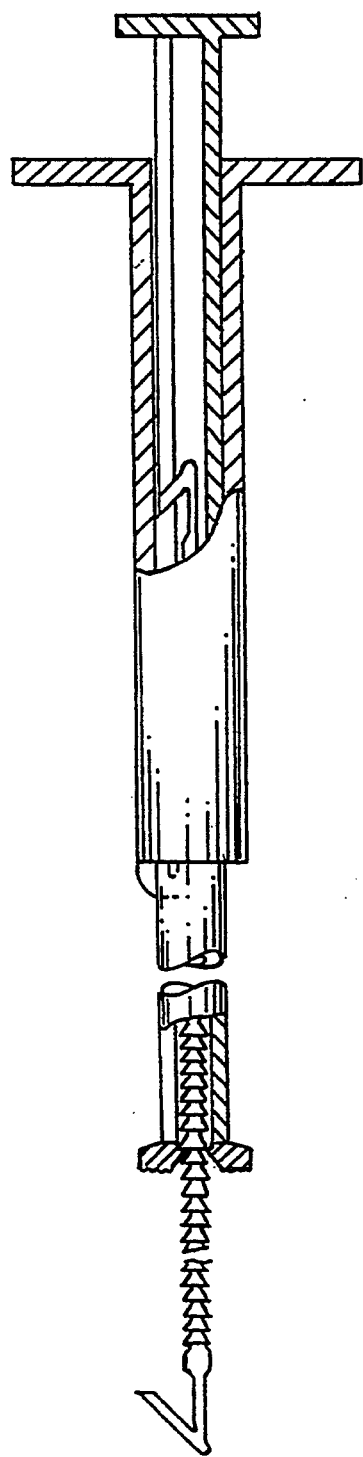
FIG. 10 is an elevational, partially cut-away view of the installation tool of FIG. 8 wherein the clamp pin of FIG. 1 has been inserted and secured in place for installation.

FIG. 10 shows the clamp pin 12 of the invention after insertion into the installation tool 80 and anchoring of its proximal hook 28 onto the retaining clip 58 in the barrel. As more particularly seen in the detailed view of FIG. 11, the wing 30 is engaged by the retaining clip 58 and prevented from moving forward by the acute angle formed by the clip's face 60 with the wall of the barrel. Moreover, the wing 30 is prevented from sliding off the retaining clip in lateral motion because the sides 78 of the groove 74 in the piston 70 sliding along the ridge 54 provide a retaining channel that keeps the wing 30 hooked to the clip 58. Moreover, the wing 30 cannot rotate proximally to any significant extent (by increasing its angle with the pin shaft much beyond 45 degrees) because the proximal tip of the hook 28 impinges on the bottom inside surface of groove 74, thus counteracting the levering force of the tip 32 of wing 30. Note that the smaller cross-section of the leg 25 of the proximal hook 28 provides a weak point within the apparatus of the invention that is outside the bone of a patient. Therefore, if the clamp pin 10 should fail under stress while it is being installed in a bone, the breakage would occur outside the surgical site and either the clamp could still be installed by other means or it could be removed in its entirety.

As illustrated in the detailed view of FIG. 12, the shaft 72 of the piston can be extended out of the barrel 52 of the installation tool to push against the clamp button 40 and force it to slide one by one over the resilient peripheral notches 26. Because of the firm connection between the retaining clip and the proximal wing in the clamp pin, the pin cannot move forward and the clamp button can be pushed with the necessary force required to effect its advancement through the plurality of notches. This feature makes it possible to easily clamp fractured bones under operating conditions that require relatively great force to be exerted on the clamp in order to create compression between approximated bone segments. This feature constitutes a great improvement over existing clamps which tend to separate from the installation tool under pressure.

Figure 15:
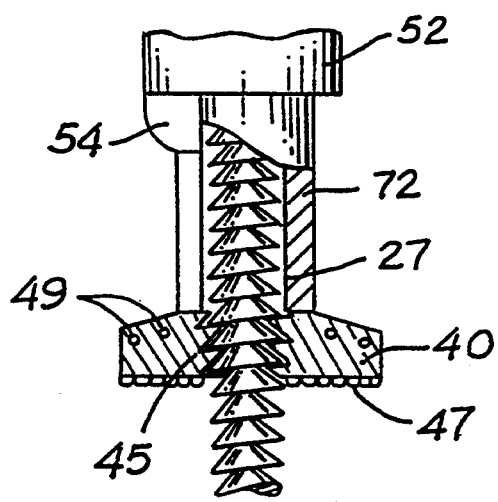
FIG. 15 is an enlarged, partially sectioned view of a threaded embodiment of the peripheral notches and the clamp button of the invention.

In another embodiment of the invention illustrated in FIG. 15, the peripheral notches of the clamp pin are constructed in helical form to produce buttress-form screw threads 27 and the resilient inner lip in the clamp button consists of a corresponding buttress-form thread 45, so as to provide a screwable connection between the two in addition to the slidable ratchet-fashion connection available through the resilient properties of the components. Thus, the clamp button may be pushed in the distal direction by the action of the piston 72 and/or, at the surgeon's option, it may be screwed manually to further tighten the clamp against a bone.

In use, this invention permits the clamping of parts of bone with minimally invasive surgery. The clamp pin is mounted in the installation tool by first taking the piston portion out of the barrel. The proximal hook of the clamp pin is introduced into the bottom of the barrel and is hooked to the retaining clip along the inside wall of the barrel. Then, the piston is introduced into the barrel from the top making sure that the retaining clip is inserted into the piston's groove, thus trapping the proximal hook of the clamp in place. The clamp is now firmly mounted in the installation tool.

Figures 16, 17:
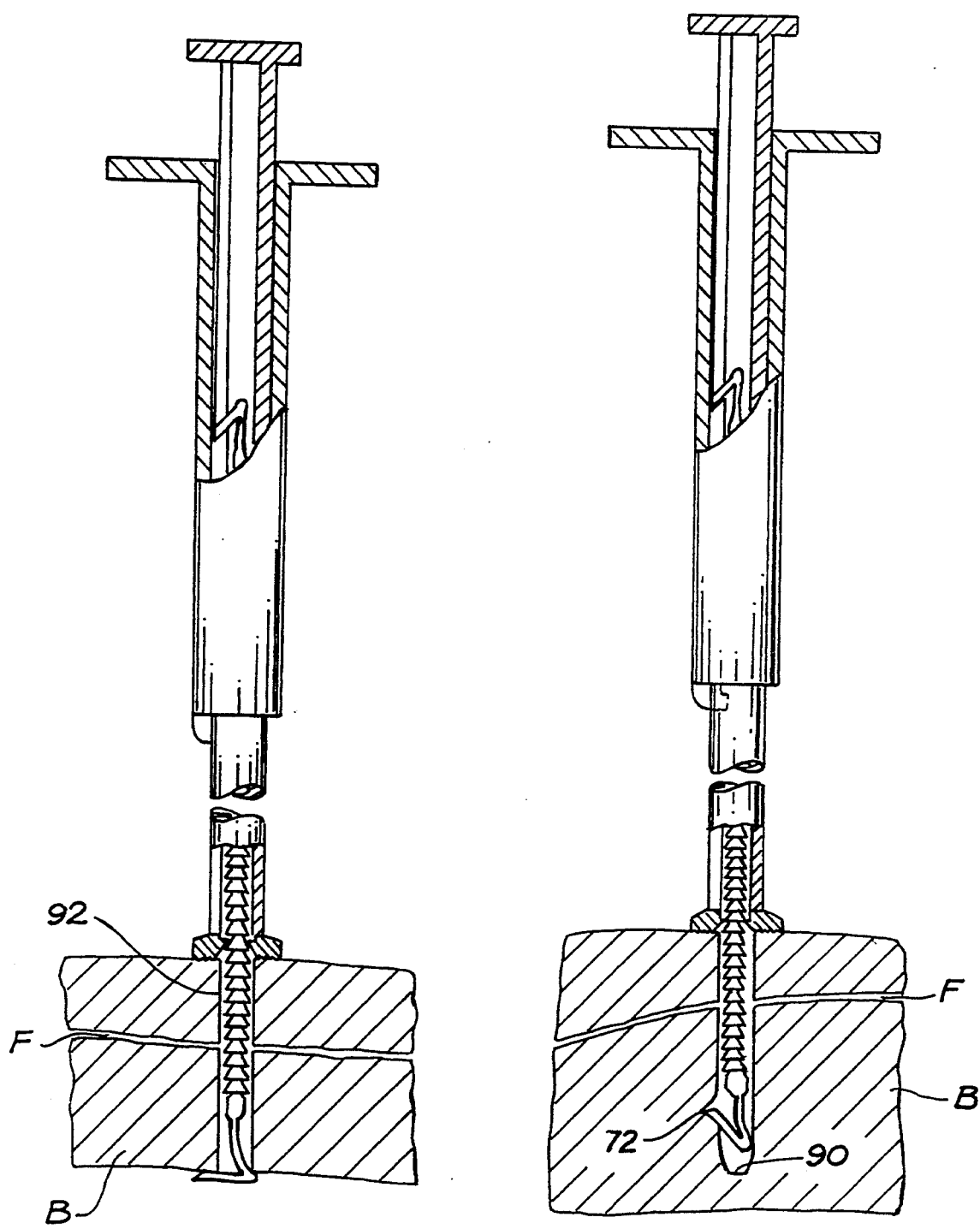
FIG. 16 is an elevational view of the bone clamp and installation tool of the invention illustrating a clamp being formed in a blind hole in a fractured bone, which is shown in cross-section.
FIG. 17 is an elevational view of the bone clamp and installation tool of the invention illustrating a clamp being formed in a through-hole in a fractured bone, which is shown in cross-section.

A straight through-hole is drilled into the bone sufficiently large to permit the introduction of the clamp pin 12 by forcing the wing 18 inward toward the pin. Because of its rounded tip 24, the pin can easily be pushed into a hole causing the bending of the wing without the tip getting caught on the inside wall of the hole. Also, because of the geometry of the contact surface 20 and the sharp edge 22, the distal hook 16 may be anchored in a blind hole 90 in a bone B by having the sharp edge engage the cancellous portion of the bone, as illustrated in FIG. 16, rather than having to drill the bone through the distal cortex. Thus, a surgeon needs only to drill the hole 90 past the fracture F and the distal hook 16 is in position to provide an anchor to form a clamp as the clamp button 40 is tightened against the proximal cortex of the bone. As seen in the figure, when the clamp button is tightened by the pulling action exerted by the installation tool's barrel on the shaft 14, the sharp edge 22 of the wing 18 digs into one side of the relatively soft cancellous bone tissue and causes the hook to bend and the distal tip 24 to make contact with the opposite side of the hole, so as to lodge the distal hook 16 in a firm anchoring position. As in the case of the bone clamp and installation tool described in the cited patents, the clamp button 40 is pressed against the bone's proximal cortex by pushing the piston 70 forward with respect to the barrel 50, in the same way that the plunger of a syringe is compressed to void its barrel. Because of the novel proximal hook in the clamp pin and the conforming retention clip in the barrel of the installation tool, the clamp button can be pushed with great force without causing the separation of the clamp pin from the tool. In addition, the connection between the two is also more firm and rigid than previously known, which facilitates the introduction of the clamp pin into the hole drilled in the bone and the manipulation of the device in a limited space. After the bone clamp is installed, the proximal portion of the shaft 14 is severed as close as possible to the clamp button, leaving the clamp in place to hold the bone parts together. As illustrated in FIG. 15, suture holes 49 may be provided in the clamp button for use by a surgeon to attach surrounding tissue to the bone clamp of the invention.

Alternatively, the various parts of bone to be clamped together may be drilled through with a straight hole 92 and the distal hook of the invention may be threaded through the hole to emerge past the distal cortex of the bone, as illustrated in FIG. 17. In that case the wing 18 is engaged by the distal surface of the bone and forms a T-like anchor by the wing bending outwardly (to the left in the illustration) and the rounded tip moving to the right in the illustration when pulled by the ratchet action (or screwable action, as applicable) of the clamp button.

When used in its helicoidal configuration, the bone clamp of the invention provides a means for tightening the clamp gradually for fine adjustments, rather than only in discrete increments. In fact, the threads can be used in ratchet fashion for step increments during the initial advancement of the clamp button toward the proximal surface of the bone, leaving the continuous screwable adjustments for the final tensioning of the clamp.

All embodiments described herein may be implemented with any of the materials currently in use for implant construction, both of the absorbable and non-absorbable type. While the embodiments shown in the figures feature the specific shapes therein described, the invention can obviously take other shapes with equivalent functionality and utility. In fact, any shape for any of the components that retains the functional characteristics described above provides an acceptable apparatus to practice the invention. Thus, various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatus and methods.

We claim:

1. A bone clamping device, comprising:
   (a) an elongated clamp pin consisting of a shaft having a proximal end for mounting on an installation tool and having a distal end for passing through a hole in a bone;
   (b) a distal hook consisting of a resilient distal wing attached to the distal end of said shaft and forming an acute angle therewith, so that said distal wing may provide a distal bone-engagement means for clamping the bone;
   (c) a proximal hook consisting of a proximal wing attached to the proximal end of said shaft and forming an acute angle therewith, so that said proximal wing may provide a means for firmly attaching the bone clamping device to the installation tool;
   (d) a plurality of resilient, peripheral notches disposed along said shaft, wherein each notch has a flat surface perpendicular to said shaft facing the distal end of the shaft and has a sloped surface facing the proximal end of the shaft; and
   (e) a clamp button having a central bore with a resilient inner lip capable of engaging said flat surface of each of said peripheral notches to prevent the button from sliding in the proximal direction, while the button is capable of resiliently sliding over said sloped surface of each notch to move in ratchet fashion toward the distal end of the shaft to provide a proximal bone-engagement means for clamping the bone;
   wherein said clamp pin and said clamp button consist of two separate components.

2. The bone clamping device recited in claim 1, wherein said distal wing forms an angle of approximately 45 degrees with said shaft and has a substantially flat contact surface normal to the shaft.

3. The bone clamping device recited in claim 1, wherein said distal end further comprises a tip substantially coaxial with said distal wing and protruding on the side of the shaft opposite to the wing.

4. The bone clamping device recited in claim 1, wherein each of said plurality of resilient peripheral notches is substantially circumferential.

5. The bone clamping device recited in claim 4, wherein each of said substantially circumferential notches disposed along said shaft is shaped like a longitudinal section of a cone having a smaller cross-section approximately the size of the shaft facing said proximal end and having a larger cross-section facing said distal end of the shaft.

6. The bone clamping device recited in claim 1, wherein said clamp button is annular and has a central bore with a resilient inner lip.

7. The bone clamping device recited in claim 1, wherein said clamp button further comprises friction bumps for increasing the adhesion of the button with the proximal surface of the clamped bone.

8. The bone clamping device recited in claim 1, wherein said proximal wing forms an angle of approximately 45 degrees with said shaft.

9. The bone clamping device recited in claim 1, wherein said proximal hook comprises a rigid wing, a resilient leg, and is smaller than said distal hook, so that the proximal wing can be folded shut to permit the insertion of the clamp pin through the central bore in said clamp button.

10. The bone clamping device recited in claim 1, wherein said peripheral notches are constructed in helical form to produce buttress-form screw threads and wherein the resilient inner lip in said clamp button consists of a buttress-form thread, so as to provide a screwable connection between the notches and the button in addition to the slidable ratchet-fashion connection available through the resilient properties of the inner lip and the peripheral notches.

11. The bone clamping device recited in claim 1, wherein said clamp button further comprises a plurality of spikes for causing soft tissue to adhere to the surface of a bone.

12. A bone clamp installation tool for an elongated clamping device having a proximal end for connection with the tool, having a distal end for passing through a hole in a bone and for providing a distal bone-engagement means, and having a proximal bone-engagement means slidably mounted thereon, said tool comprising:

(a) a barrel consisting of a hollow tube having an inside wall between an upper end and a lower end thereof, said tube containing a keel-like longitudinal ridge protruding inward from said inside wall in the bottom portion of the barrel, wherein said ridge forms a retaining clip having a contact face oriented toward said upper end of the tube and disposed at an acute angle with said inside wall of the tube, so as to cooperatively engage the proximal end of the clamping device; and (b) a piston consisting of a hollow shaft with an outside diameter slightly smaller than the inside diameter of said tube so that the barrel and the piston can be slidably connected to form a syringe-type assembly, wherein said shaft has a longitudinal groove sized to fit snugly around the longitudinal ridge in said barrel;

wherein said piston is sufficiently long to enable a user to push the proximal bone-engagement means slidably mounted on the clamping device as far as required during use.

13. The tool recited in claim 12, further comprising a rounded push-knob attached to a top portion of said piston for pushing the piston forward through the barrel.

14. The tool recited in claim 12, further comprising a forked retaining tab protruding inwardly from a lower end of said ridge to provide a guide for the clamping device mounted thereon.

15. The tool recited in claim 12, further comprising a handle attached to a top portion of said barrel for holding the installation tool.

16. The tool recited in claim 12, wherein said contact face is disposed at an angle of approximately 45 degrees with said inside wall of the tube.

17. The tool recited in claim 12, wherein said tube and said shaft are cylindrical.

18. The tool recited in claim 12, wherein said longitudinal ridge in the barrel is approximately half the length of the barrel.

19. An apparatus for installing a bone clamp through a hole in a bone, wherein a bone clamping device is attached to an installation tool, said apparatus comprising:

(a) a clamping device that comprises:
  (1) an elongated clamp pin consisting of a shaft having a proximal end for mounting on the installation tool and having a distal end for passing through a hole in a bone;
  (2) a distal hook consisting of a resilient distal wing attached to the distal end of said shaft and forming an acute angle therewith, so that said distal wing may provide a distal bone-engagement means for clamping the bone;
  (3) a proximal hook consisting of a proximal wing attached to the proximal end of said shaft and forming an acute angle therewith, so that said proximal wing may provide a means for firmly attaching the bone clamping device to the installation tool;
  (4) a plurality of resilient, peripheral notches disposed along said shaft, wherein each notch has as flat surface perpendicular to said shaft facing the distal end of the shaft and has a sloped surface facing the proximal end of the shaft; and
  (5) a clamp button having a central bore with a resilient inner lip capable of engaging said flat surface of each of said peripheral notches to prevent the button from sliding in the proximal direction, while the button is capable of resiliently sliding over the sloped surface of each notch to move in ratchet fashion toward the distal end of the shaft to provide a proximal bone-engagement means for clamping the bone;
wherein said clamp pin and said clamp button consist of two separate components; and (b) an installation tool that comprises:
  (1) a barrel consisting of a hollow tube having an inside wall between an upper end and a lower end thereof, said tube containing a keel-like longitudinal ridge protruding inward from said inside wall in the bottom portion of the barrel, wherein said ridge forms a retaining clip having a contact face oriented toward said upper end of the tube and disposed at an acute angle with said inside wall of the tube, so as to cooperatively engage said proximal wing of the clamping device; and (2) a piston consisting of a hollow shaft with an outside diameter slightly smaller than the inside diameter of said tube so that the barrel and the piston can be slidably connected to form a syringe-type assembly, wherein said shaft has a longitudinal groove sized to fit snugly around the longitudinal ridge in said barrel;

wherein said piston is sufficiently long to enable a user to push the proximal bone-engagement means slidably mounted on the clamping device as far as required during use.

20. The bone clamping device recited in claim 19, wherein said distal wing forms an angle of approximately 45 degrees with said shaft and has a substantially flat contact surface normal to the shaft; wherein said proximal wing forms an angle of approximately 45 degrees with said shaft; wherein each of said plurality of resilient peripheral notches is substantially circumferential and is shaped like a longitudinal section of a cone having a smaller cross-section approximately the size of the shaft facing said proximal end and having a larger cross-section facing said distal end of the shaft; wherein said clamp button is annular and has a central bore with a resilient inner lip and comprising friction bumps for increasing the adhesion of the button with the proximal surface of the clamped bone; and wherein said proximal hook is resilient and is smaller than said distal hook, so that the proximal wing can be folded shut to permit the insertion of the clamp pin through the central bore in said clamp button.

21. The bone clamping device recited in claim 17, wherein said peripheral notches are constructed in helical form to produce buttress-form screw threads and wherein the resilient inner lip in said clamp button consists of a buttress-form thread, so as to provide a screwable connection between the notches and the button in addition to the slidable ratchet-fashion connection available through the resilient properties of the inner lip and the peripheral notches.

* * * * *